United States Patent [19]
Shi et al.

[11] Patent Number: 5,981,249
[45] Date of Patent: Nov. 9, 1999

[54] SINGLE-CHAIN POLYPEPTIDES COMPRISING CREATINE KINASE M AND CREATINE KINASE B

[75] Inventors: Qinwei Shi, Etobicoke; Rowel Tobias, Mississauga, both of Canada

[73] Assignee: Spectral Diagnostics, Inc., Toronto, Canada

[21] Appl. No.: 09/018,760

[22] Filed: Feb. 5, 1998

[51] Int. Cl.[6] .............................. C12N 9/12; C12N 15/00; C12N 1/20; C07H 21/04
[52] U.S. Cl. .................. 435/194; 435/320.1; 435/252.3; 435/325; 536/23.2
[58] Field of Search ................................ 435/194, 320.1, 435/325, 252.3; 536/23.1, 23.2

[56] References Cited

U.S. PATENT DOCUMENTS

| | | | |
|---|---|---|---|
| 4,624,916 | 11/1986 | Shah et al. | 435/7 |
| 4,900,662 | 2/1990 | Shah et al. | 435/7 |
| 4,946,778 | 8/1990 | Ladner et al. | 435/69.9 |
| 5,321,030 | 6/1994 | Kaddurah-daouk et al. | 514/275 |
| 5,369,006 | 11/1994 | Obzansky | 435/7.4 |
| 5,395,754 | 3/1995 | Lambotte et al. | 435/607.4 |
| 5,496,716 | 3/1996 | Brandt | 435/188 |
| 5,516,637 | 5/1996 | Huang et al. | 435/6 |

FOREIGN PATENT DOCUMENTS

| | | |
|---|---|---|
| 384130 | 8/1990 | European Pat. Off. . |
| WO 91/01498 | 2/1991 | WIPO . |
| 18019 | 5/1991 | WIPO . |
| 12662 | 5/1995 | WIPO . |

OTHER PUBLICATIONS

Schafer et al., J.Cell.Biol., 106, 1161–1169, Apr. 1988.
Lindbladh et al., Biochemistry, 33, 11684–11689, Jul. 1994.
Cook and Wood, 1994, J Immunol Meth, 171:227–37.
Friedman et al, 1993, Clinical Chemistry, 39:1598–601.
Grenadier et al. (1983) Am. Heart J. 105:408–16.
Hoberg et al. (1987) Eur. Heart J. 8:989–94.
Hu et al, 1996, Protein Expression and Purification, 7:289–93.
Lee et al. (1986) Ann. Intern. Med. 105:221–33.
Lee et al. (1987) Arch. Intern. Med. 147:115–21.
Lindbladh et al, 1994, Biochemistry, 33:11692–8.
Seguin et al. (1988) J. Thorac. Cardiovasc. Surg. 95:294–7.
Speicher et al. (1983) In: Choosing effective lab. tests, W.B.Saunders Com., Philadelphia, pp. 155–163.

*Primary Examiner*—Ponnathapura Achutamurthy
*Assistant Examiner*—Maryam Monshipouri
*Attorney, Agent, or Firm*—Klauber & Jackson

[57] ABSTRACT

This invention relates to single-chain polypeptides and their genetic sequences comprising creatine kinase M and creatine kinase B. The single-chain polypeptide may be expressed recombinantly. A linker peptide may be interposed between the creatine kinase sequences. A linker peptide of about 6 to about 50 amino acids is preferred. The single-chain polypeptide has utility as a control or calibrator for creatine kinase MB assays, for the purification of creatine kinase antibodies, and as an antigen for the preparation of antibodies.

14 Claims, No Drawings

SINGLE-CHAIN POLYPEPTIDES COMPRISING CREATINE KINASE M AND CREATINE KINASE B

FIELD OF THE INVENTION

This invention relates to recombinantly-expressed, single-chain polypeptides comprising creatine kinase subunits M and B, and their corresponding genetic sequences, and transformed microorganisms carrying the sequences and expressing the polypeptides.

BACKGROUND OF THE INVENTION

Early and accurate assessment of suspected acute myocardial infarction is critically dependent on the sensitive and specific detection and quantitation in blood, serum or plasma of released cardiac muscle intracellular components in order to distinguish a potentially lethal event in need of emergency measures from non-life threatening conditions such as angina and non-cardiac chest pain such as dyspepsia. Early electrocardiographic changes are neither adequately specific nor sensitive, and the medical profession has come to rely on serum biochemical markers of cardiac tissue injury for early diagnosis. Among the markers released into the circulation from heart tissue following injury or necrosis, creatine kinase MB (CK-MB) is indicative of a cardiac event and is used diagnostically to identify patients undergoing a heart attack.

Lee and Goldman (1986, Annals of Internal Medicine 105:221–233) provide a discussion of the utility of CK-MB in the diagnosis of acute myocardial infarction. Creatine kinase is a dimeric enzyme that catalyzes the transfer of high-energy phosphate groups and is found predominantly in tissues that consume large amounts of energy. The enzyme has two subunits, each of which can be either type M (for muscle) or B (for brain), thus, three combinations exist: MM, MB, and BB. The CK-MM isoenzyme is dominant in adult skeletal muscle, whereas CK-BB is found mostly in the central nervous system. In humans, heart muscle tissue creatine kinase is about 85% MM and 15% MB. In order to specifically identify muscle injury of cardiac origin, quantitation of only the CK-MB isoenzyme in circulation is desirable.

The amino acid sequence differences between the M and B isoenzymes are exploited in diagnostic tests which specifically measure the cardiac isoenzyme CK-MB. Rapid diagnostic tests employing cardiac markers including CK-MB are described, for example, in U.S. Pat. Nos. 5,604,105 and 5,290,678. These and other procedures offer the rapidity of diagnosing myocardial infarction in the emergency room setting and offer significant medical benefit for patients. Numerous other procedures for measuring CK-MB are available, such as automatic clinical analyzers, column chromatography, radioimmunoassay, and electrophoretic methods. Diagnostic tests developed to measure the level of CK-MB in bodily fluids frequently utilize CK-MB as an antigen for the preparation of antibodies used in the assay procedure, as well as purified CK-MB used as controls and calibrators in performing the assay. Assay calibrators are used to prepare a series of dilutions by which a standard curve across the operating range of an assay is prepared; assay controls are used to confirm that an assay is operating properly by ensuring that the assayed values of pre-determined samples fall within an acceptable range around their labeled values. In order for the assay to be calibrated properly, the CK-MB controls and calibrators must remain stable and in a form which is immunodetectable by the antibody or antibodies used in the assay procedure. Rapid diagnostic tests for CK-MB likewise may utilize a positive control to ensure accurate operation of the test.

Numerous CK-MB preparations from both natural and recombinant sources have been described. U.S. Pat. No. 5,496,716 describes a stabilized CK-MB composition comprising serum protein plus a CK-MB enzymatic substrate (for example, ATP or creatine) with or without a CK-MB enzymatic product (for example, ADP or phosphocreatine). Stability with a less than a 10% loss by immunoassay after 27 days at room temperature was claimed. Recombinant human CK-MB has been expressed in COS cells as a dimer (Friedman et al., 1993, Clinical Chemistry 39:1598–1601): the subunits were expressed as separate proteins then formed non-covalent dimers within the cells. Medix Biotech Inc. presently offers for sale a recombinant CK-MB product.

However, preparation of CK-MB from natural sources is a tedious procedure involving many steps including protein isolation from tissue, with its attendant hazards of infection, and protein purification, with its attendant risks of potential degradation and variable recovery, to provide an isolated CK-MB material of suitable quality and quantity for use as a calibrator or control. CK-MB prepared by recombinant methods involves the expression of separate M and B isoforms and their subsequent association to form the MB dimer which, whether performed in vitro or occurring within a host cell expressing both isoforms, will result in the formation of the MM, BB, and MB dimer; the MB dimer must be subsequently purified from the other dimers. This subsequent protein purification caries the same potential problems as described above.

Thus, there exists a need for stable CK-MB calibrators and controls that are easy to prepare and purify, and will meet the requirements of the industry. As will be evident below, a principal object of the present invention is to provide a stable CK-MB preparation for assay and other uses which comprises the CK-M subunit and the CK-B subunit on a single polypeptide chain, prepared as a recombinant construct and expressed in a bacterial expression system as a single polypeptide. A single-chain polypeptide of this invention comprising human creatine kinase M and creatine kinase B is stable, readily purified, uncontaminated with the MM or BB dimers, and has utility for the aforementioned purposes. Moreover, the product is easily produced by the skilled artisan. This ease of production maximizes the reproducibility of the products of the invention.

SUMMARY OF THE INVENTION

It is a principal objective of the present invention to provide a single-chain polypeptide comprising creatine kinase M and creatine kinase B. The presence of creatine kinase M and creatine kinase B on the same polypeptide chain confers conformational stability and immunostability to the product. The single-chain polypeptide may preferably include a linker sequence interposed between the sequence of creatine kinase M and that of creatine kinase B. The sequence of the linker peptide is chosen based on known structural and conformational contributions of peptide segments so that it does not interfere with the tertiary structure of the product and therefore its aforementioned utilities. A single-chain polypeptide in which creatine kinase M and creatine kinase B are joined, optionally through a linker peptide, provides a stable, reproducible, and easily purified material for the development of CK-MB assays, an antigen for preparing CK-MB antibodies, as well as material for use as controls and calibrators for CK-MB assays. Furthermore, there is no contamination of the preparation with CK-MM or CK-BB isoenzymes.

The single-chain polypeptide of the present invention is prepared most readily by recombinant techniques, by constructing a replicable cloning or expression vehicle such as a plasmid carrying the genetic sequence for the single-chain polypeptide, and transforming a host cell, such as *E. coli*, with the vehicle or plasmid, and expressing the polypeptide in the host cell. The single-chain CK-MB construct preferably contains a genetic sequence for a linker peptide sequence interposed between the creatine kinase M and creatine kinase B nucleotide sequences, the sequence introduced by recombinant means. Certain modifications may be made in the genetic sequence of the gene which codes for creatine kinase molecules, with or without changes in the consequent amino acid sequence of the polypeptide, in order to improve the expression of the polypeptide in the host cell. These changes do not alter the utility of the single-chain polypeptide for use in the aforementioned purposes.

It is another object of the present invention to provide a genetic sequence for a single-chain polypeptide comprising the genetic sequences of creatine kinase M and creatine kinase B. The genetic sequence may also include a linker genetic sequence interposed between the genetic sequences of creatine kinase M and creatine kinase B. A host cell may be transformed with the replicable cloning or expression vehicle containing the aforementioned genetic sequence.

It is a further object of the present invention to provide a host cell containing a replicable cloning or expression vehicle such as a plasmid carrying the genetic sequence for a single-chain polypeptide chain comprising the genetic sequences of creatine kinase M and creatine kinase B, and capable of expressing a single-chain polypeptide comprising creatine kinase M and creatine kinase B, with or without a linker.

These and other aspects of the present invention will be better appreciated by reference to the following drawings and Detailed Description.

DETAILED DESCRIPTION OF THE INVENTION

Measurement in circulation of the cardiac muscle-associated enzyme creatine kinase MB has proven to be an early and specific indicator of suspected acute myocardial infarction. As such, methods for rapidly and accurately detecting creatine kinase MB in blood have been and are being developed for diagnosing heart attack in an emergency situation, and countless lives have been and will be saved as a result. However, in order to develop accurate and dependable diagnostic assays and to ensure the validity of these assays using assay controls and calibrators, the availability of stable, high-quality human creatine kinase MB controls and calibrators is critical for quality control and testing purposes, as well as CK-MB antigens for raising antibodies for assays.

The present invention provides a single-chain polypeptide comprising human creatine kinase M and creatine kinase B. The creatine kinase subunits are thus covalently linked and reside on the same linear polypeptide chain. This polypeptide provides a stable CK-MB to meet the needs of the industry. The single-chain polypeptide may be prepared by recombinant techniques, and preferably includes a linker polypeptide sequence interposed between the creatine kinase M and creatine kinase B sequences. The length and sequence of this linker sequence is limited only in that it does not interfere with the immunodetectability of the product and its other aforementioned utilities. A preferred linker comprises 6 to 50 amino acids.

For example, one embodiment of the single-chain creatine kinase MB polypeptide may comprise the creatine kinase M sequence at the N-terminal portion of the polypeptide, with the C-terminus of the creatine kinase M sequence engaged in a peptide bond with the N-terminus of the creatine kinase B sequence. In a second and presently preferred embodiment, a linker peptide sequence is interposed between the creatine kinase M and the creatine kinase B amino acid sequences. Another possible arrangement comprises the creatine kinase M sequence at the N-terminal portion of the polypeptide, its C-terminus engaged in a peptide bond with the N-terminus of the linker peptide, and the C-terminus of the linker peptide then engaged in a peptide bond with the N-terminus of the creatine kinase B sequence. An example of this construct is the amino acid sequence depicted in SEQ ID NO:4. Amino acid residues 1 through 381 comprise creatine kinase M, residues 382–400 comprise the linker peptide sequence, and residues 401–780 comprise creatine kinase B. In this example, the amino acid sequence of the linker is represented in SEQ ID NO:2. It contains 19 amino acids.

The amino acid sequences in the above examples correspond to the nucleotide sequences of the cDNA coding for these polypeptides. The genetic sequence in the first example comprises the creatine kinase M genetic sequence at the 5' half of the cDNA, its 3' end followed immediately by the 5' half of the creatine kinase B genetic sequence. In the preferred embodiment wherein a linker is interposed between the creatine kinase M and creatine kinase B sequences, the 5' of the cDNA sequence begins with the creatine kinase M genetic sequence, its 3' end followed by the 5' end of the optional interposed linker genetic sequence, and its 3' end followed by the 5' end of the creatine kinase B genetic sequence, ending at the 3' end of the creatine kinase B cDNA. In the specific example above, the genetic sequence is represented in SEQ ID NO:3. Nucleotides 1 through 1142 (amino acid residues 1–381) code for creatine kinase M, nucleotides 1143 through 1200 (residues 382–400) code for the linker peptide sequence, and nucleotides 1201 through 2340 (residues 401–780) code for creatine kinase B. The cDNA sequence of the linker alone is presented in SEQ ID NO:1.

As described above, selection of the length and specific sequence of the optional linker polypeptide is limited only in that it must not interfere with the immunodetectability of the single-chain creatine kinase MB polypeptide. It is believed that with a suitable linker sequence, the creatine kinase M and creatine kinase B segments of the single polypeptide chain associate with each other in a similar fashion as they do in the naturally-occurring, non-covalently-bound dimer of creatine kinase M and creatine kinase B, and the attachment of the subunits in the single polypeptide chain maintains the conformation of the association and thus the consistent immunodetectability of the CK-MB. Within this preferred embodiment, a linker of about 6 to about 50 amino acids (and a corresponding number of nucleotides in the genetic sequence) is preferred, for ease and economics of preparation.

It is preferred to produce the single-chain creatine kinase MB polypeptide of this invention with a relatively short linker segment because with such products, there is little or no interference with the tertiary structure of the product. Hence there is little or no interference with the availability of epitopes for reaction with readily-available antibodies.

For example, a useful linker polypeptide sequence comprises $(Gly_4Ser)_3$ which provides a flexible peptide sequence that allows the two subunits to associate. In order to construct the genetic sequence with a linker, an additional 2 codons at each end of the linker are present, which were needed in order to provide unique restriction sites to create the genetic construct of the desired single-chain polypeptide. In one example, codons corresponding to Thr-Ser at the N-terminus of the linker and Ala-Cys at the C-terminus, may be included. Thus, a suitable 19-residue linker may be prepared (genetic sequence SEQ ID NO:1 and peptide SEQ ID NO:2).

Known and well-understood recombinant methods may be used to prepare the DNA sequence comprising the creatine kinase subunits and the optional linker sequence and to introduce the sequence into a host cell, and standard expression methods are used to express and purify the recombinant polypeptide. These methods are similar to those used for the preparation of fusion proteins such as that described for the two metabolically-coupled yeast enzymes, citrate synthase and malate dehydrogenase (Lindbladh et al., Biochemistry 33:11692–11698 [1994]); in the preparation of fusion proteins for phage display (U.S. Pat. No. 5,516,637); and in the preparation of single-chain polypeptides comprising the antigen-binding site of antibodies (U.S. Pat. No. 4,946,778). Coincidentally, the latter invention describes the preparation of a single-chain antigen-binding polypeptide that specifically recognizes creatine kinase MB, a product unrelated to the present invention.

In the instance in which no linker sequence is desired, the creatine kinase M and creatine kinase B nucleotide sequences may be joined through suitable techniques known in the art such as the SOEing method using pairs of partially overlapping primers, for example, as described by Hu et al. (1996, Protein Expression and Purification 7:289–293) in which rare codons in human cardiac troponin T were replaced with synonymous major codons. These methods are well known to the skilled artisan.

The recombinant construct is prepared as an expression or cloning vehicle, or plasmid, and introduced into a host cell for expression. Methods for expression of recombinant proteins are known in the art. Once expressed, the single-chain polypeptide may be purified by standard protein purification methods.

Several CK-MB assays are commercially available, all of which operate using different formats, instruments, and assay controls and calibrators. Example include the Stratus (R) immunoassay analyzer from Dade, Access(R) from Sanofi, and IMX(R) from Abbott.

A single-chain polypeptide of this invention comprising creatine kinase M and creatine kinase B may also be used for the purification of proteins and other substances including antibodies with an affinity for binding creatine kinase M, creatine kinase B, and creatine kinase MB. For example, the single-chain polypeptide of the present invention with or without a linker may be covalently bound to an insoluble matrix or polymer and situated in a chromatography column. A cell or tissue extract suspected of containing a material that binds CK-MB, or an antibody preparation raised against CK-MB, may be passed through the column, whereby it would adhere to the covalently-bound polypeptide. After washing the matrix, the adherent material may be eluted by changing the pH of the eluting buffer or other standard methods used in protein purification.

A single-chain polypeptide of the present invention may also be useful for the preparation of monoclonal or polyclonal anti-CK-MB antibodies, using standard methods of animal immunization or hybridoma preparation.

The single-chain polypeptide of the present invention comprising creatine kinase M and creatine kinase B has utility for the preparation of sensitive CK-MB assays and for the calibration of such assays. As will be seen from the following non-limiting examples, the single-chain polypeptide exhibits superior performance when compared to other CK-MB calibrators.

Example 1

Expression of a Single-chain Creatine Kinase MB Polypeptide in *E. coli*

Full-length human creatine kinase M and creatine kinase B subunit cDNAs were amplified by polymerase chain reaction (PCR) from human heart and human brain Quick-clone cDNA libraries (Clontech) using specific primers designed from the published sequences. Creatine kinase M cDNA was linked with creatine kinase B through a linker sequence having SEQ ID:1 by use of the following restriction sites: Creatine kinase M: 5', NdeI, 3', SpeI; creatine kinase B: 5', SphI, 3', NotI. The construct, with genetic and polypeptide sequences of SEQ ID NO:3 and SEQ ID NO:4, respectively, was inserted into a pET21 (Novagen) expression vector and *E. coli* BL21(DE3)(Novagen) was transformed.

*E. coli* cells were harvested and lysed following standard procedures. Inclusion bodies containing insoluble single-chain CK-MB were solubilized in 8 M urea and the resulting suspension incubated with chaperonin extract. The CK-MB-chaperonin mixture was allowed to refold by step-dialysis and the addition of coupling buffer. The renatured crude extract was purified by a single-step immunoaffinity chromatography procedure using an immobilized monoclonal antibody to CK-MB, CK-MM, or CK-BB. Single-chain CK-MB polypeptide was eluted with diethylamine.

The above purification procedure was accomplished in 3.5 days, in comparison to 5 days by conventional expression and isolation in which both the M and B subunits were expressed within a single cell. Recombinant CK-MB dimers were isolated from MM and BB dimers that also formed in the host cell using affinity purification employing a specific anti-CK-MB monoclonal antibody. Furthermore, the yield of the single-chain polypeptide of the present invention was 160 mg per liter of *E. coli* culture, as compared with 50 mg per liter from the conventionally expression CK-MB. In addition, electrophoretic analysis showed no contamination of the single-chain polypeptide preparation with CK-MM or CK-BB isoenzymes, as would be expected, though the purified CK-MB prepared by conventional recombinant methods followed by purification of the MB isoenzyme was contaminated with both CK-MM and CK-BB isoenzymes.

The *E. coli* strain expressing the single-chain creatine kinase MB polypeptide as described above has been deposited on Feb. 11, 1998, with the American Type Culture Collection, 10801 University Boulevard, Manassas Va. 20110-2209, and has been designated ATCC number 98648.

Example 2

Immunodetectability of the Single-Chain Creatine Kinase MB Polypeptide

The single-chain CK-MB described in Example 1 was assayed using the Stratus(R) Immunoassay Analyzer. Immunoreactivity per unit mass was increased by 60% as compared with the conventionally-prepared recombinant CK-MB.

While the invention has been described and illustrated herein by references to the specific embodiments, various specific material, procedures and examples, it is understood that the invention is not restricted to the particular material combinations of material, and procedures selected for that purpose. Indeed, various modifications of the invention in addition to those described herein will become apparent to those skilled in the art from the foregoing description and the accompanying sequences. Such modifications are intended to fall within the scope of the appended claims.

Various citations to prior publications are mentioned throughout this specification, each of which is incorporated herein by reference in its entirety.

---

What is claimed is:

1. A polynucleotide which codes for an immunostable single-chain polypeptide comprising creatine kinase M joined by a peptide linker sequence to creatine kinase B.

2. A replicable cloning or expression vehicle comprising the polynucleotide of claim 1.

3. The vehicle of claim 2 which is a plasmid.

4. A host cell transformed with a vehicle of claim 2.

5. An *E. coli* transformed with a replicable cloning or expression vehicle comprising the polynucleotide of claim 1.

6. The polynucleotide of claim 1 identified as (SEQ ID NO:3).

7. A replicable cloning or expression vehicle carrying the sequence set forth in (SEQ ID NO:3).

8. A host cell transformed with the vehicle of claim 7.

9. The host cell of claim 8 which is *E. coli*.

10. The *E. coli* of claim 9 which is deposited with the American Type Culture Collection and designated ATCC number 98648.

11. The polynucleotide of claim 1 wherein the linker polynucleotide comprises from about 18 to about 150 nucleotides.

12. An immunostable single chain polypeptide comprising creatine kinase M joined by a peptide linker sequence to creatine kindise B.

13. The polypeptide of claim 12 having an amino acid sequence as set forth in (SEQ ID NO:4).

14. The polypeptide of claim 12 wherein the peptide linker sequence comprises from about 6 to about 50 amino acids.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 57 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (ix) FEATURE:
      (A) NAME/KEY: CDS
      (B) LOCATION: 1..57

(xi) SEQUENCE DESCRIPTION: SEQ ID NO:1:

```
ACT AGT GGT GGT GGT GGT TCT GGT GGG GGG GGT TCT GGT GGC GGT GGT        48
Thr Ser Gly Gly Gly Gly Ser Gly Gly Gly Gly Ser Gly Gly Gly Gly
 1               5                  10                  15

TCT GCA TGC                                                            57
Ser Ala Cys
```

(2) INFORMATION FOR SEQ ID NO:2:

(i) SEQUENCE CHARACTERISTICS:
      (A) LENGTH: 19 amino acids
      (B) TYPE: amino acid
      (D) TOPOLOGY: linear (ii) MOLECULE TYPE: protein (xi) SEQUENCE DESCRIPTION: SEQ ID NO:2:

```
Thr Ser Gly Gly Gly Gly Ser Gly Gly Gly Gly Ser Gly Gly Gly Gly
 1               5                  10                  15

Ser Ala Cys
```

(2) INFORMATION FOR SEQ ID NO:3:

(i) SEQUENCE CHARACTERISTICS:
      (A) LENGTH: 2343 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (xi) SEQUENCE DESCRIPTION: SEQ ID NO:3:

```
ATGCCATTCG GTAACACCCA CAACAAGTTC AAGCTGAATT ACAAGCCTGA GGAGGAGTAC        60

CCCGACCTCA GCAAACATAA CAACCACATG GCCAAGGTAC TGACCCTTGA ACTCTACAAG       120
```

```
AAGCTGCGGG ACAAGGAGAT CCCATCTGGC TTCACTGTAG ACGATGTCAT CCAGACAGGA      180

GTGGACAACC CAGGTCACCC CTTCATCATG ACCGTGGGCT GCGTGGCTGG TGATGAGGAG      240

TCCTACGAAG TTTTCAAGGA ACTCTTTGAC CCCATCATCT CGGATCGCCA CGGGGGCTAC      300

AAACCCACTG ACAAGCACAA GACTGACCTC AACCATGAAA ACCTCAAGGG TGGAGACGAC      360

CTGGACCCCA ACTACGTGCT CAGCAGCCCG GTCCGCACTG GCCGCAGCAT CAAGGGCTAC      420

ACGTTGCCCC CACACTGCTC CCGTGGCGAG CGCCGGGCGG TGGAGAAGCT CTCTGTGGAA      480

GCTCTCAACA GCCTGACGGG CGAGTTCAAA GGGAAGTACT ACCCTCTGAA GAGCATGACG      540

GAGAAGGAGC AGCAGCAGCT CATCGATGAC CACTTCCAGT TCGACAAGCC CGTGTCCCCG      600

CTGCTGCTGG CCTCAGGCAT GGCCCGCCAC TGGCCCGACG CCCCTGGCAT CTGGCACAAT      660

GACAACAAGA GCTTCCTGGT GTGGGTGAAC GAGGAGGATC ACCTCCGGGT CATCTCCATG      720

GAGAAGGGGG GCAACATGAA GGAGGTTTTC CGCCGCTTCT GCGTAGGGCT GCAGAAGATT      780

GAGGAGATCT TTAAGAAAGC TGGCCACCCC TTCATGTGGA ACCAGCACCT GGGCTACGTG      840

CTCACCTGCC CATCCAACCT GGGCACTGGG CTGCGTGGAG GCGTGCATGT GAAGCTGGCG      900

CACCTGAGCA AGCACCCCAA GTTCGAGGAG ATCCTCACCC GCCTGCGTCT GGAGAAGAGG      960

GGTACAGGTG CGGTGGACAC AGCTGCCGTG GGCTCAGTAT TTGACGTGTC CAACGCTGAT     1020

CGGCTGGGCT CGTCCGAAGT AGAACAGGTG CAGCTGGTGG TGGATGGTGT GAAGCTCATG     1080

GTGGAAATGG AGAAGAAGTT GGAGAAAGGC CAGTCCATCG ACGACATGAT CCCCGCCCAG     1140

AAGACTAGTG GTGGTGGTGG TTCTGGTGGG GGGGGTTCTG GTGGCGGTGG TTCTGCATGC     1200

CCCTTCTCCA ACAGCCACAA CGCACTGAAG CTGCGCTTCC CGGCCGAGGA CGAGTTCCCC     1260

GACCTGAGCG CCCACAACAA CCACATGGCC AAGGTGCTGA CCCCCGAGCT GTACGCGGAC     1320

GTGCGCGCCA AGAGCACGCC GAGCGGCTTC ACGCTGGACG ACGTCATCCA GACAGGCGTG     1380

GACAACCCGG GCCACCCGTA CATCATGACC GTGGGCTGCG TGGCGGGCGA CGAGGAGTCC     1440

TACGAAGTGT TCAAGGATCT CTTCGACCCC ATCATCGAGG ACCGGCACCG GCGCTACAAG     1500

CCCAGCGATG ACGACAAGAC CGACCTCAAC CCCGACAACC TGCAGGGCGG CGACGACCTG     1560

GACCCCAACT ACGTGCTGAG CTCGCGGGTG GCCACGGGCC GCAGCATCCG TGGCTTCTGC     1620

CTCCCCCCGC ACTGCAGCCG CGGGGAGCGC CGAGCCATCG AGAAGCTCGC GGTGGAAGCC     1680

CTGTCCAGCC TGGACGGCGA CCTGGCGGGC CGATACTACG CGCTCAAGAG CATGACGGAG     1740

GCGGAGCAGC AGCAGCTCAT CGACGACCAC TTCCTCTTCG ACAAGCCCGT GTCGCCCCTG     1800

CTGCTGGCCT CGGGCATGGC CCGCGACTGG CCCGACGCCG CGCGTATCTG GCACAATGAC     1860

AATAAGACCT TCCTGGTGTG GGTCAACGAG GAGGACCACC TGCGGGTCAT CTCCATGCAG     1920

AAGGGGGGCA ACATGAAGGA GGTGTTCACC CGCTTCTGCA CCGGCCTCAC CCAGATTGAA     1980

ACTCTCTTCA GTCTAAGGA CTATGAGTTC ATGTGGAACC CTCACCTGGG CTACATCCTC     2040

ACCTGCCCAT CCAACCTGGG CACCGGGCTG CGGGCAGGTG TCGATATCAA GCTGCCCAAC     2100

CTGGGCAAGC ATGACAAGTT CTCGGAGGTG CTTAAGCGGC TGCGACTTCA GAAGCGAGGC     2160

ACAGGCGGTG TGGACACGGC TGCGGTGGGC GGGGTCTTCG ACGTCTCCAA CGCTGACCGC     2220

CTGGGCTTCT CAGAGGTGGA GCTGGTGCAG ATGGTGGTGG ACGGAGTGAA GCTGCTCATC     2280

GAGATGGAAC AGCGGCTGGA GCAGGGCCAG GCCATCGACG ACCTCATGCC TGCCCAGAAA     2340

TGA                                                                   2343
```

-continued (2) INFORMATION FOR SEQ ID NO:4:

(i) SEQUENCE CHARACTERISTICS:
        (A) LENGTH: 780 amino acids
        (B) TYPE: amino acid
        (C) STRANDEDNESS: single
        (D) TOPOLOGY: linear (ii) MOLECULE TYPE: protein (iii) HYPOTHETICAL: NO (ix) FEATURE:
        (A) NAME/KEY: CDS
        (B) LOCATION: 1..2343

(xi) SEQUENCE DESCRIPTION: SEQ ID NO:4:

```
Met Pro Phe Gly Asn Thr His Asn Lys Phe Lys Leu Asn Tyr Lys Pro
 1               5                  10                  15

Glu Glu Glu Tyr Pro Asp Leu Ser Lys His Asn Asn His Met Ala Lys
                20                  25                  30

Val Leu Thr Leu Glu Leu Tyr Lys Lys Leu Arg Asp Lys Glu Ile Pro
            35                  40                  45

Ser Gly Phe Thr Val Asp Asp Val Ile Gln Thr Gly Val Asp Asn Pro
 50                  55                  60

Gly His Pro Phe Ile Met Thr Val Gly Cys Val Ala Gly Asp Glu Glu
 65                  70                  75                  80

Ser Tyr Glu Val Phe Lys Glu Leu Phe Asp Pro Ile Ile Ser Asp Arg
                85                  90                  95

His Gly Gly Tyr Lys Pro Thr Asp Lys His Lys Thr Asp Leu Asn His
                100                 105                 110

Glu Asn Leu Lys Gly Gly Asp Asp Leu Asp Pro Asn Tyr Val Leu Ser
            115                 120                 125

Ser Pro Val Arg Thr Gly Arg Ser Ile Lys Gly Tyr Thr Leu Pro Pro
130                 135                 140

His Cys Ser Arg Gly Glu Arg Arg Ala Val Glu Lys Leu Ser Val Glu
145                 150                 155                 160

Ala Leu Asn Ser Leu Thr Gly Glu Phe Lys Gly Lys Tyr Tyr Pro Leu
                165                 170                 175

Lys Ser Met Thr Glu Lys Glu Gln Gln Gln Leu Ile Asp Asp His Phe
            180                 185                 190

Gln Phe Asp Lys Pro Val Ser Pro Leu Leu Leu Ala Ser Gly Met Ala
        195                 200                 205

Arg His Trp Pro Asp Ala Pro Gly Ile Trp His Asn Asp Asn Lys Ser
210                 215                 220

Phe Leu Val Trp Val Asn Glu Glu Asp His Leu Arg Val Ile Ser Met
225                 230                 235                 240

Glu Lys Gly Gly Asn Met Lys Glu Val Phe Arg Arg Phe Cys Val Gly
                245                 250                 255

Leu Gln Lys Ile Glu Glu Ile Phe Lys Lys Ala Gly His Pro Phe Met
            260                 265                 270

Trp Asn Gln His Leu Gly Tyr Val Leu Thr Cys Pro Ser Asn Leu Gly
        275                 280                 285

Thr Gly Leu Arg Gly Gly Val His Val Lys Leu Ala His Leu Ser Lys
290                 295                 300

His Pro Lys Phe Glu Glu Ile Leu Thr Arg Leu Arg Leu Glu Lys Arg
305                 310                 315                 320
```

-continued

```
Gly Thr Gly Ala Val Asp Thr Ala Ala Val Gly Ser Val Phe Asp Val
            325                 330                 335

Ser Asn Ala Asp Arg Leu Gly Ser Ser Glu Val Glu Gln Val Gln Leu
            340                 345                 350

Val Val Asp Gly Val Lys Leu Met Val Glu Met Glu Lys Lys Leu Glu
            355                 360                 365

Lys Gly Gln Ser Ile Asp Asp Met Ile Pro Ala Gln Lys Thr Ser Gly
            370                 375                 380

Gly Gly Gly Ser Gly Gly Gly Ser Gly Gly Gly Ser Ala Cys
385                 390                 395                 400

Pro Phe Ser Asn Ser His Asn Ala Leu Lys Leu Arg Phe Pro Ala Glu
            405                 410                 415

Asp Glu Phe Pro Asp Leu Ser Ala His Asn Asn His Met Ala Lys Val
            420                 425                 430

Leu Thr Pro Glu Leu Tyr Ala Asp Val Arg Ala Lys Ser Thr Pro Ser
            435                 440                 445

Gly Phe Thr Leu Asp Asp Val Ile Gln Thr Gly Val Asp Asn Pro Gly
            450                 455                 460

His Pro Tyr Ile Met Thr Val Gly Cys Val Ala Gly Asp Glu Glu Ser
465                 470                 475                 480

Tyr Glu Val Phe Lys Asp Leu Phe Asp Pro Ile Ile Glu Asp Arg His
            485                 490                 495

Arg Arg Tyr Lys Pro Ser Asp Asp Lys Thr Asp Leu Asn Pro Asp
            500                 505                 510

Asn Leu Gln Gly Gly Asp Asp Leu Asp Pro Asn Tyr Val Leu Ser Ser
            515                 520                 525

Arg Val Ala Thr Gly Arg Ser Ile Arg Gly Phe Cys Leu Pro Pro His
            530                 535                 540

Cys Ser Arg Gly Glu Arg Arg Ala Ile Glu Lys Leu Ala Val Glu Ala
545                 550                 555                 560

Leu Ser Ser Leu Asp Gly Asp Leu Ala Gly Arg Tyr Tyr Ala Leu Lys
            565                 570                 575

Ser Met Thr Glu Ala Glu Gln Gln Gln Leu Ile Asp Asp His Phe Leu
            580                 585                 590

Phe Asp Lys Pro Val Ser Pro Leu Leu Leu Ala Ser Gly Met Ala Arg
            595                 600                 605

Asp Trp Pro Asp Ala Ala Arg Ile Trp His Asn Asp Asn Lys Thr Phe
            610                 615                 620

Leu Val Trp Val Asn Glu Glu Asp His Leu Arg Val Ile Ser Met Gln
625                 630                 635                 640

Lys Gly Gly Asn Met Lys Glu Val Phe Thr Arg Phe Cys Thr Gly Leu
            645                 650                 655

Thr Gln Ile Glu Thr Leu Phe Lys Ser Lys Asp Tyr Glu Phe Met Trp
            660                 665                 670

Asn Pro His Leu Gly Tyr Ile Leu Thr Cys Pro Ser Asn Leu Gly Thr
            675                 680                 685

Gly Leu Arg Ala Gly Val Asp Ile Lys Leu Pro Asn Leu Gly Lys His
            690                 695                 700

Asp Lys Phe Ser Glu Val Leu Lys Arg Leu Arg Leu Gln Lys Arg Gly
705                 710                 715                 720

Thr Gly Gly Val Asp Thr Ala Ala Val Gly Val Phe Asp Val Ser
            725                 730                 735
```

```
Asn Ala Asp Arg Leu Gly Phe Ser Glu Val Glu Leu Val Gln Met Val
            740                 745                 750

Val Asp Gly Val Lys Leu Leu Ile Glu Met Glu Gln Arg Leu Glu Gln
        755                 760                 765

Gly Gln Ala Ile Asp Asp Leu Met Pro Ala Gln Lys
    770                 775                 780
```